United States Patent [19]

Toyota et al.

[11] Patent Number: 4,697,210

[45] Date of Patent: Sep. 29, 1987

[54] ENDOSCOPE FOR DISPLAYING A NORMAL IMAGE

[75] Inventors: Makoto Toyota; Fumitaka Takeshita; Satoshi Arakawa, all of Omiya, Japan

[73] Assignee: Fuji Photo Optical Co., Ltd., Japan

[21] Appl. No.: 766,298

[22] Filed: Aug. 16, 1985

[30] Foreign Application Priority Data

Aug. 20, 1984 [JP] Japan .................................. 59-172796

[51] Int. Cl.⁴ .............................................. H04N 7/18
[52] U.S. Cl. .......................................... 358/98; 128/4; 128/6
[58] Field of Search ...................... 358/98, 113; 128/4, 128/6

[56] References Cited

U.S. PATENT DOCUMENTS 4,399,458 8/1983 Berry et al. .......................... 358/113
4,475,539 10/1984 Konomura ............................. 128/6
4,573,450 3/1986 Arakawa ............................... 128/6

Primary Examiner—Howard W. Britton
Assistant Examiner—John K. Peng
Attorney, Agent, or Firm—Parkhurst & Oliff

[57] ABSTRACT

An endoscope used for observing the interior of a cavity in a human body. In the endoscope according to the present invention, an image sensor is provided in the forward end of an insertion section and an object of interest is displayed on a screen of a television set in response to a video signal obtained from the image sensor. According to the present invention, image information from the image sensor is provisionally stored in a memory, and the read-out from the memory is performed by horizontal scanning in accordance with readout information by reversing the steps in the case of the write-in. With this arrangement, an image of the object of interest, which is inverted in an optical system in the forward end of the insertion section of the endoscope, can be displayed on the screen of the television as a normal image.

9 Claims, 5 Drawing Figures

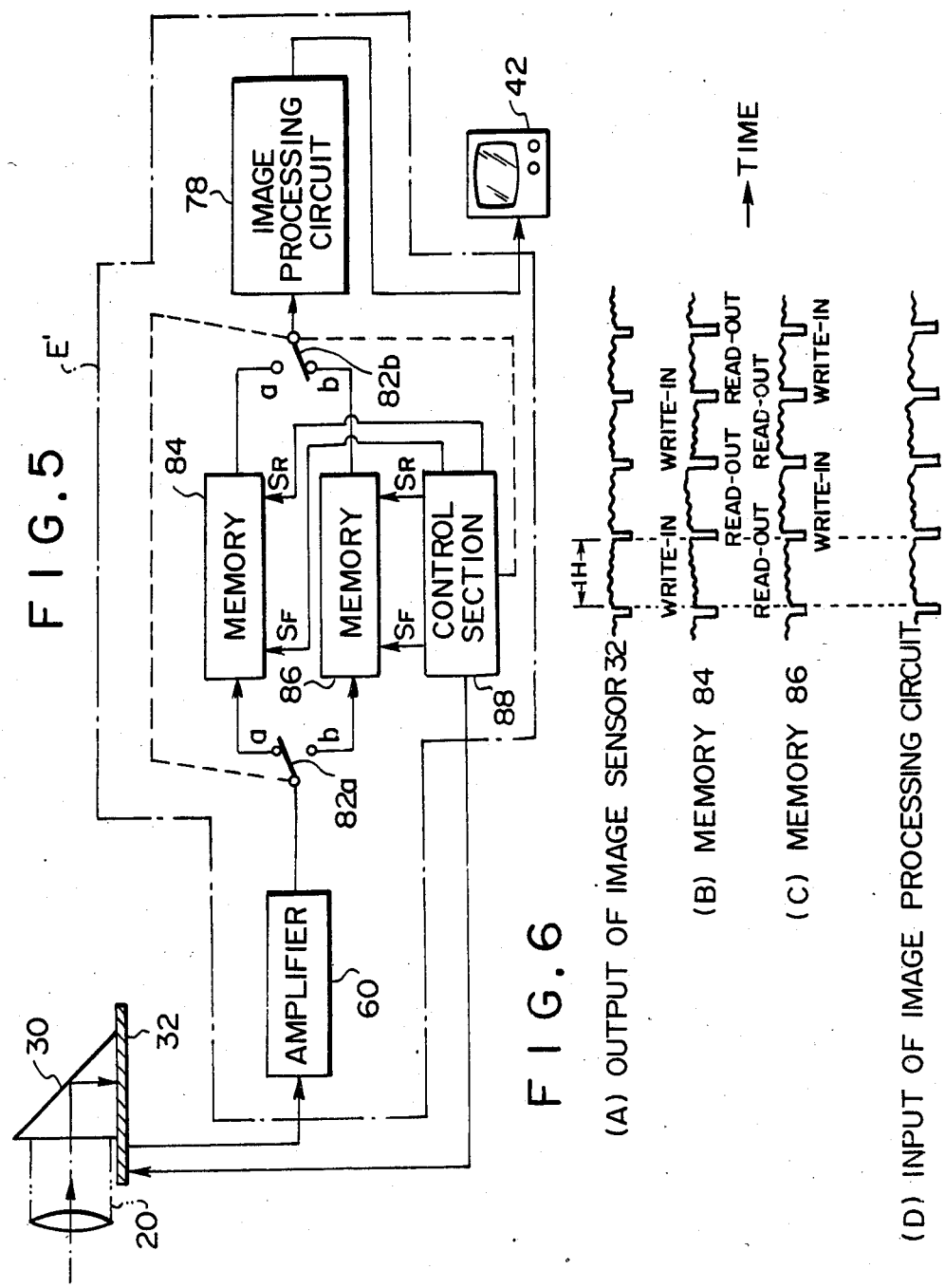

ENDOSCOPE FOR DISPLAYING A NORMAL IMAGE

BACKGROUND OF THE INVENTION

1. Field of the Invention

This invention relates to endoscopes, and more particularly, to an endoscope wherein a plate shaped image sensor as an imaging device is provided in the forward end portion of an insertion section and image information from the imaging device is processed to be displayed on a monitor television set.

2. Description of the Prior Art

In addition to the conventional endoscope using a so called optical fiber bundle as an image guide, there has been proposed a television endoscope utilizing a plate shaped image sensor wherein matrix-arranged very small light receiving members are combined with a charge transfer device represented by a charge coupled device. For example, as shown in FIG. 1, there has been proposed a television endoscope comprising an insertion section A provided in the forward portion thereof with a coupled charge device, a manual control section B, aconnecting section C, a connector D, a controller E and a monitor television set F. The television endoscope of the type described is advantageous as compared the conventional endoscope using image guide fibers in that the former is high in durability, can apply various processes to electric signals as being video outputs and is economical in the cost, whereby to put it to practical use is studied now.

Now, the face plate shaped image sensor used as the forward end imaging device of the television endoscope has been made considerably compact in size due to the recent improvements in the techniques of manufacture and in the degree of integration. However, it cannot be said that the image sensor is sufficiently compact in size for the application to the endoscope. The reason is that, as well known, in order to be inserted into a cavity in a living body, the outer diameter of the endoscope must be small. For example, the outer diameter of a gastroscope may preferably be about 10 mm or less. Further, even if the provided image sensor is satisfactorily small in size, on the other hand, such demands are made that the resolution should be improved, i.e. the number of picture elements on the image sensor should be increased. These demands word in the direction of increasing the image sensor in size more or less.

Under the above described background, in constructing the so-called television endoscope, it becomes an important point to arrange how spatially efficiently the forward end construction of the endoscope, particularly, an image sensor or an objective optical system for making an optical image to focus at the image sensor.

What is proposed to solve this problem is the forward end construction of the television endoscope shown in FIGS. 2 and 3.

FIGS. 2 and 3 show one example applied to a direct vision type endoscope in a sectional side view of the forward end portion and in a schematic front view, respectively. As shown in FIG. 2, a forward end portion 10 of an insertion section A of the endoscope is constituted by a forward end rigid portion 12 and a flexible portion 14. The forward end rigid portion 12 is formed of a forward fitment 16 and cannot be curved. The flexible portion 14 is formed of a plurality of articular rings 18 connected to one another and can be curved vertically and laterally by a well known control wire.

As shown in FIG. 3, inserted through the forward end portion 10 of the endoscope in the longitudinal direction (from the right to the left in FIG. 2) are a light guide channels 22 (24), a forceps channel 26 and an air-water supply channel 28 in addition to an objective optical system 20. As apparent from FIG. 2, the objective optical system 20 has an arrangement of a plurality of lenses, in general. In the rear portion thereof, there is provided a rectangular prism 30 which changes the directions of a light path of the objective optical system 20 through 90° and a rectangular plate shaped image snesor 32 is jointed to a light emitting surface of the rectangular prism 30.

The image sensor 32 is positioned close to a plane incorporating a longitudinal center axis (a line X—X in FIG. 2 and a line XI—XI in FIG. 3) of the endoscope, so that the outer diameter of the endoscope can be effectively utilized. The forward fitment 16 is formed with openings in accordance with other various channels. For example, connected to the forceps channel 26 as shown in FIG. 2 is a forceps tube 36, into which a forceps is inserted for use. As apparent from FIGS.2 and 3, a base 38 of the image sensor 32 is slightly longer than the image sensor 32 in the widthwise direction (the direction of the diameter of the insertion section of the endoscope), and is generally equal in length to the image sensor 32 in the longitudinal direction (the longitudinal direction of the insertion section of the endoscope). A lead wire 40 of the image sensor 32 is connected to the base 38 and further connected to a control terminal and an output terminal of the image sensor 32. The lead wire 40 delivers a driving signal from a driving circuit of the controller E to the image sensor 32 and delivers a video signal from the image sensor to the controller E.

However, the endoscope shown in FIG. 2 uses the prism 30 in the objective optical system thereof, whereby the object of interest is made to focus on a surface of the imaging device with the right and left sides thereof being inverted. Because of this, in the endoscope of this type, the image of the object of interest on the monitor television set disadvantageously becomes an image with the right and left sides thereof being inverted.

SUMMARY OF THE INVENTION

The present invention has been developed to obviate the disadvantages of the prior art and has as its object the provision of an endoscope wherein an image displayed on a monitor television set is displayed as a normal image identical with an image of an object of interest.

To this end, the present invention contemplates that image information from an imaging device is provisionally stored in a memory, and the read-out from the memory is performed by reversing the steps in the case of the write-in.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and wherein:

FIG. 5 is a block diagram showing another embodiment of the present invention; and FIG. 6 is a waveform chart of action of the respective portions in the embodiment shown in FIG. 5.

DETAILED DESCRIPTION OF THE INVENTION

Detailed description will hereunder be given of the preferred embodiment of the endoscope according to the present invention with reference to the accompanying drawings.

Figure 1:
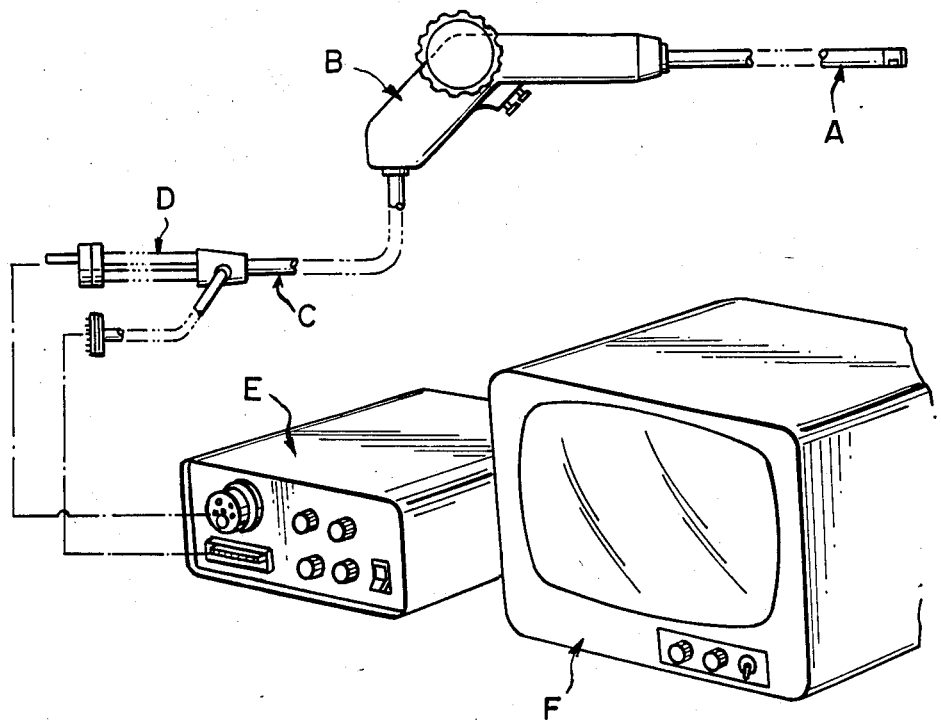
FIG. 1 is a schematic block diagram showing the television endoscope.
Figure 2:
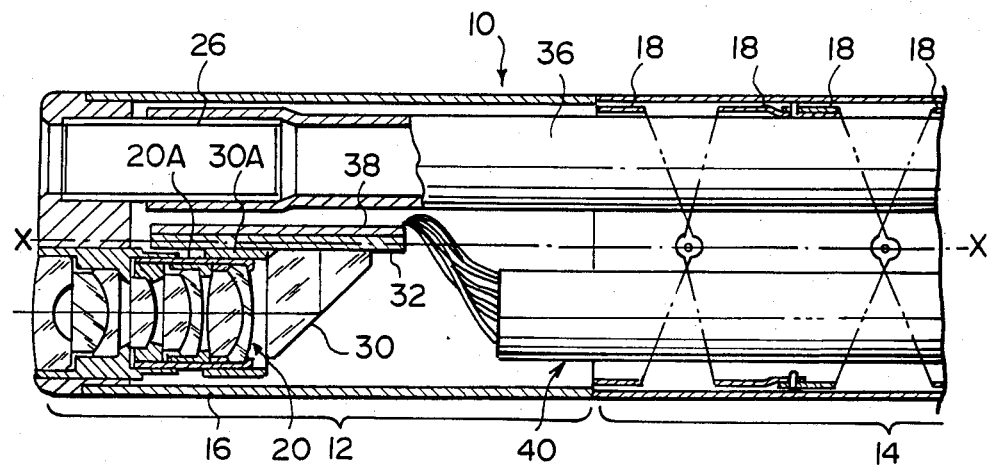
FIG. 2 is a sectional side view showing the insertion section of the direct vision type television endoscope.
Figure 3:
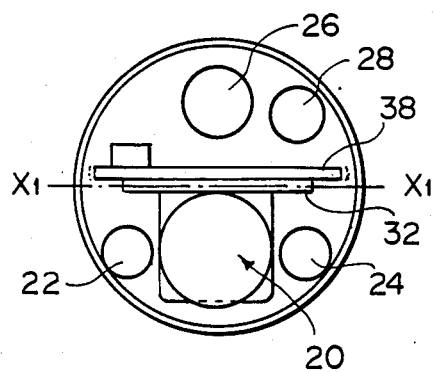
FIG. 3 is a schematic front view thereof.
Figure 4:
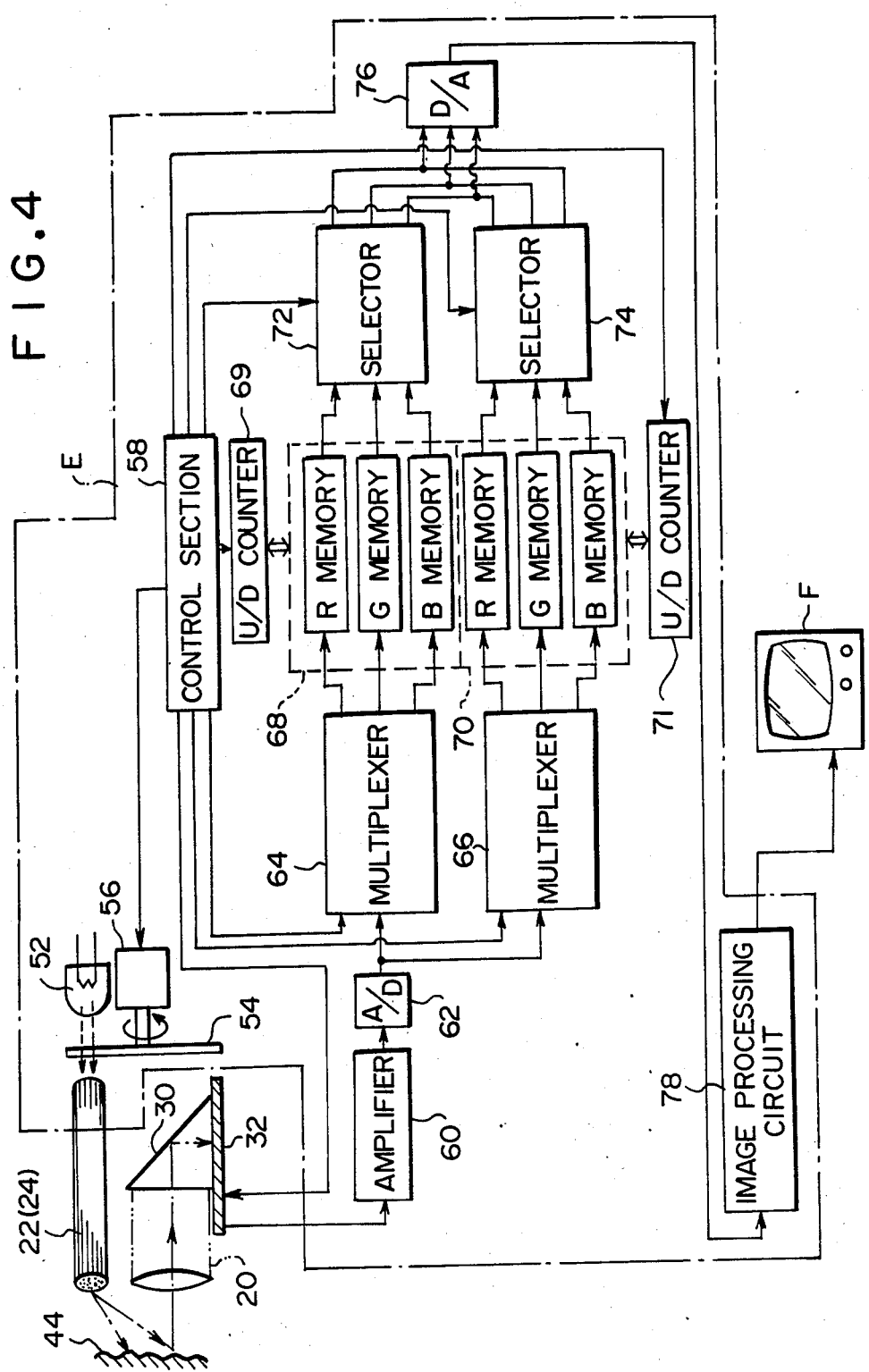
FIG. 4 is a block diagram showing one embodiment of the present invention.

FIG. 4 is a block diagram showing one embodiment of the present invention.

In the controller E, a light source 52 for supplying the light to a light guide 22 (24) is opposed to one end of the light guide. Between the light source 52 and the light guide 22 (24), there is provided a rotary color filter 54, on which filters of three colors including R(red), G(green) and B(blue) are arranged at intervals of 120° (or intervals of $\frac{1}{3}$ n: where n is an integer), whereby the light from the light source 52 are successively changed into colored lights including R, G and B. The rotary color filter 54 is driven by a motor 56 and the rotational speed is controlled by a control section 58. The object of interest 44 irradiated by the light guide 22 (24) is made to focus on the image sensor 32 by an objective optical system 20. An image signal obtained by photo-electro-transducing this image is inputted to an amplifier 60 through the connecting section C, where the image signal is amplified to a predetermined level. An analogue output from the amplifier 60 is converted into a digital signal by an analogue-digital (A/D) converter 62. Connected in parallel to the A/D converter 62 are multiplexers 64 and 66, to which are respectively connected memory sections 68 and 70 each constituted by three block memories for storing image signals of R, G and B. Every time the storing of data for one horizontal scanning time duration into the memory section 68 or 70 connected to the multiplexers 64 or 66 is completed, the multiplexers 64 and 66 are switched to each other by the control section 58, and image information of R, G and B is stored into the corresponding memory of the memory section 68 (or 70) in synchronism with the rotation of the three color filter 54.

Respectively connected to the memory sections 68 and 70 are updown (U/D) counters 69 and 71 for performing the addressing of the memory blocks to carry out the write-in and the read-out. When one of the U/D counters is used for the write-in, the other is used for the read-out, during the write-in, the counter acts as the up counter, whereas, during the read-out, the counter acts as the down counter. The determination as to which modes the counters act in is made in the control section 58 and commands are outputted to the respective U/D counters 69 and 71. During the read-out, due to down counts, image data are outputted form the address opposite to the write-in, whereby the right and left sides of the image become opposite to the input data. More specifically, the image picked up by the image sensor 32 in such a manner that the right and left sides are inverted is inverted, when the image is read out of the memory section 68 or 70, the image is turned into a normal image. Output signals from the respective memory blocks of the memory sections 68 and 70 are outputted to selectors 72 and 74. These selectors 72 and 74 act alternately. While the multiplexer 64 is operated, the selector 74 acts, and, while the multiplexer 66 is operated, the selector 72 acts. The selectors 72 and 74 function as switches and, during operation, output the input signals to output terminals as they are. Output terminals identical in color with each other in the selectors 72 and 74 are connected to each other in parallel, and further, connected to input terminals of the D/A converter 76.

The image information successively outputted from the selector 72 or 74 is converted into an analogue signal by the D/A converter 76. The analogue signal is inputted to an image processing circuit 78 connected to the D/A converter 76, where respective signals of R, G and B are composed and processed into predetermined transfer modes. Output signals from the image processing circuit 78 are outputted to the monitor television set F, where an image of the object of interest is displayed as a normal image.

In the above-described arrangement, the light from the light source 52 is colored by the rotary filter 54 in the order of R→G→B, passed through the connecting section C and the light guide of the control section B, and irradiates the object of interest 44 as the lighting from the forward end of the forward end section 10. The object of interest thus irradiated is made to focus on a pickup surface of the image sensor with the right and left sides being inverted, by the objective optical system 20 through the prism 30. This image is taken out by the image sensor 32 as an electric signal, amplified by the amplifier 60, and thereafter, outputted to the A/D converter 62. The A/D converter 62 converts analogue video information into digital information and outputs the same to the multiplexers 64 and 66 in the order of R, G and B. During the initial write-in, only the multiplexer 64 is operated, and each of R, G and B video information for one horizontal scanning time duration, which is outputted from the A/D converter 62, is successively stored into an R memory, G memory and B memory of the memory section 68. In this case, the U/D counter 69 acts as the up counter and specifics storage addresses while successively adding the address numbers. During the succeeding horizontal scanning time duration, the multiplexer 66 is operated, whereby the signals of R, G and B are successively written in the addresses specified by the U/D counter 71 in the respective blocks of the memory section 69. Simultaneously, the selector 72 is selected and the U/D counter 69 acts as the down counter, whereby image data of R, G and B are read out by the memory section 68 and outputted to the D/A converter 76 through the selector 72. Upon completion of the read-out from the memory section 68 and completion of the write-in into the memory section 70, the multiplexer 64 is turned on again and the multiplexer 66 is turned off, the write-in into the memory section 68 is begun, the selector 72 is switched to the selector 74, and data are read out of the memory section 70 (At this time, the U/D counter 69 acts as the up counter and the U/D counter 71 acts as the down counter). As described above, the memory sections 68 and 70 alternately repeat the write-in operations and the read-out operations, the image information outputted from the D/A converter 76 is processed into a color image, which is a mixture of three colors, by the image processing circuit 78, further, converted in signal from to NTSC (National television system committee)

method or the like, thereafter supplied to the monitor television set 42, and displayed as a normal image.

FIG. 5 is a block diagram showing another embodiment of the present invention. In the preceding embodiment, the digital memories have been used, whereas, in this embodiment, analogue memories are used. Additionally, in FIG. 5, the arrangement of supplying the lights R, G and B to the light guide is not shown, and the same reference numerals shown in FIG. 4 are used to designate same or similar parts in FIG. 5.

A double throw switch 82a is connected to an output terminal of the amplifier 60 incorporated in the controller E, and connected to respective stationary terminals a and b of the swtich 82a are analogue memories 84 and 86 using CCD, BBD (bucket bridge device) or the like, respectively. Furthermore, connected to respective read-out terminals of analogue memories 84 and 86 are stationary terminals a and b of a switch 82b operationally associated with the switch 82a. Further, a stationary terminal of this switch 82b is connected to an input terminal of the image processing circuit 78. The switches 82a and 82b are alternately switched to each other by a control section 88 with every horizontal scanning time duration. Further, the control section 88 has a function of alternately applying clock signals of two types for regulating the direction of read-out (normal direction shift pulses SF and reverse direction shift pulses SR) to the analogue memories 84 and 86 per unit of horizontal scanning time duration. Additionally, in practice, as the switches 82a and 82b, electronic switches constituted by semiconductor devices are used.

In the above-described arrangement, firstly, if the respective movable contact points of the switches 82a and 82b are in contact with the stationary contact points a and b, then an output signal from the image sensor 32 indicated by (A) in FIG. 6 is amplified by the amplifier 60, and thereafter, stored in the analogue memory 84 through the switch 82a. At this time, the normal direction shift pulses SF are delivered to the memory 84 from the control section 88. The shift pulses SF are continuously outputted with every horizontal scanning time duration (1H), signals from the amplifier 60 for one horizontal scanning time duration are stored as indicated by (B) in FIG. 6. Upon completion of the write-in for one horizontal scanning time duration, during a subsequent horizontal blanking time duration, the control section 88 changes the switches 82a and 82b over to the contact points b and a, and applies the shift pulses SR and SF to the analogue memories 84 and 86, respectively. As the result, output signals from the amplifier 60 are written into the analogu memory 86 through the switch 82a, while, data stored in the analogue memory 84, to which are applied the reverse direction shift pulses SR, are outputted to the image processing circuit 78 through the switch 82b in the reverse direction. As the result, the image data, which have been stored in such a manner that the right and left side being inverted, are read out as a normal image. Upon completion of the read-out and the write-in for one horizontal scanning time duration, the switches 82a and 82b are changed over, the shift pulses SF are applied to the memory 84, the shift pulses SR are applied to the memory 86, the write-in into the memory 84 is performed, and the read-out from the memory 86 is performed. The above-described processes are alternately repeated with every horizontal scanning time duration as indicated by (B) and (C) in FIG. 6, a normal image can be displayed on a screen of the monitor television set.

Additionally, in the foregoing description, the memory has been broadly divided into two, which are used alternately, however, desirable numbers of memory sections and analogue memories may be successively and selectively used.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. An endoscope wherein an insertion section provided at the forward end portion thereof with an objective optical system including a reflecting surface and a solid state imaging device is inserted into a portion of an object of interest and said portion of the object of interest is displayed on a screen of a display unit in response to a video signal outputted from said solid state imaging device in the forward end of said insertion section, characterized in that said endoscope comprises:

a plurality of memories, into which image information obtainable from said solid state imaging device is written;

first switching means provided on the input sides of said plurality of memories for successively switching said memories with every horizontal scanning time duration;

second switching means provided on the output sides of said plurality of memories for switching said memories with every horizontal scanning time duration such that image information is read out successively from the memory, in which the write-in is completed; and control means for writing image information into said plurality of memories in a predetermined order and for outputting a control signal to read out image information from the plurality of memories in an order opposite to the predetermined order.

2. An endoscope as set forth in claim 1, wherein said plurality of memories are digital memories.

3. An endoscope as set forth in claim 1, wherein said plurality of memories are analogue memories.

4. An endoscope as set forth in any one of claims 1 to 3, wherein a rectangular prism is provided in the rear portion of said objective optical system in the longitudinal direction of the endoscope, a light path of said objective optical system is changed through 90° and a face plate shaped imaging device is jointed to a light emitting surface of said rectangular prism.

5. An endoscope as set forth in claim 1, further comprising filters of three colors including red, green and blue for color-separating lights irradiated from a light source to the portion of the object of interest.

6. An endoscope as set forth in claim 1, wherein said plurality of memories includes an R memory, a G memory and a B memory for storing red, green and blue color image information respectively.

7. An endoscope as set forth in claim 1, wherein said control means carries out switching control of said first and second switching means such that associated color image data are written into an R memory, a G memory and a B memory of said plurality of memories in synchronism with the rotation past a light source of red, green and blue filters interposed between the light source and the object of interest.

8. An endoscope as set forth in claim 1, wherein said control means includes an updown counter for specifying memory storage addresses for image information written into and read out of said plurality of memories.

9. An endoscope wherein an insertion section provided at the forward end portion thereof with an objective optical system including a reflecting surface and a solid state imaging device is inserted into a portion of an object of interest and said portion of the object of interest is displayed on a screen of a display unit in response to a video signal outputted from said solid state imaging device in the forward end of said insertion section, characterized in that said endoscope comprises:

a plurality of memory sections, each of said memory sections comprising a plurality of memories into which image information obtainable from said solid state imaging device is written;

first switching means provided on the input sides of said plurality of memories for successively switching said memories with every horizontal scanning time duration;

second switching means provided on the output sides of said plurality of memories for switching said memories with every horizontal scanning time duration such that image information is read out successively from the memory section, in which the write-in is completed; and control means for writing image information into said plurality of memories in a predetermined order and for outputting a control signal to read out image information from the plurality of memories in an order opposite to the predetermined order.

* * * * *